United States Patent
Hong et al.

(10) Patent No.: US 9,149,502 B2
(45) Date of Patent: *Oct. 6, 2015

(54) LOW IMPURITY CONTENT CASPOFUNGIN PREPARATION, METHOD FOR PREPARING SAME, AND USE THEREOF

(71) Applicant: Shanghai Techwell Biopharmaceutical Co., Ltd., Shanghai (CN)

(72) Inventors: Yunhai Hong, Shanghai (CN); Ying Xue, Shanghai (CN); Lixin Sha, Shanghai (CN); Xiaoming Ji, Shanghai (CN)

(73) Assignee: Shanghai Techwell Biopharmaceuticals Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/346,268

(22) PCT Filed: Sep. 25, 2012

(86) PCT No.: PCT/CN2012/081951
§ 371 (c)(1),
(2) Date: Mar. 20, 2014

(87) PCT Pub. No.: WO2013/044788
PCT Pub. Date: Apr. 4, 2013

(65) Prior Publication Data
US 2014/0221274 A1    Aug. 7, 2014

(30) Foreign Application Priority Data

Sep. 26, 2011 (CN) .......................... 2011 1 0288782
Dec. 21, 2011 (CN) .......................... 2011 1 0434022

(51) Int. Cl.
*A61K 38/12* (2006.01)
*C07K 7/56* (2006.01)
*A61K 38/08* (2006.01)
*A61K 9/19* (2006.01)
*A61K 47/36* (2006.01)
*A61K 47/42* (2006.01)

(52) U.S. Cl.
CPC . *A61K 38/08* (2013.01); *A61K 9/19* (2013.01); *A61K 38/12* (2013.01); *A61K 47/36* (2013.01); *A61K 47/42* (2013.01); *C07K 7/56* (2013.01)

(58) Field of Classification Search
None
See application file for complete search history.

(56) References Cited

U.S. PATENT DOCUMENTS

| 5,952,300 A * | 9/1999 | Nerurkar et al. ............... 514/3.3 |
| 6,267,958 B1 * | 7/2001 | Andya et al. ............... 424/130.1 |
| 6,586,574 B1 * | 7/2003 | Hansen .......................... 530/384 |
| 2009/0054331 A1 * | 2/2009 | Chen et al. ....................... 514/12 |
| 2010/0137197 A1 * | 6/2010 | Mittal et al. ....................... 514/9 |

FOREIGN PATENT DOCUMENTS

| CN | 102153616 A | 8/2011 |
| CN | 102219832 A | 10/2011 |
| CN | 102488886 A | 6/2012 |
| CN | 102488889 A | 6/2012 |
| WO | 2010/008493 A2 | 1/2010 |

OTHER PUBLICATIONS

Translation of CN 102153616 A (Aug. 17, 2011).*
International Search Report corresponding to PCT/CN2012/081951 dated Jan. 3, 2013 (English Translation; 4 pages).

* cited by examiner

*Primary Examiner* — Jeffrey E Russel
(74) *Attorney, Agent, or Firm* — Kilpatrick Townsend & Stockton LLP

(57) ABSTRACT

Disclosed is a low impurity content caspofungin pharmaceutical composition and a method for preparing the low impurity content caspofungin pharmaceutical composition. The caspofungin pharmaceutical composition comprises the compound of formula I and/or a pharmaceutically acceptable salt thereof, in combination with a saccharide protective agent(s) and an amino acid(s). The caspofungin pharmaceutical composition is prepared by dissolving the saccharide protective agent and the amino acid into water or a suitable buffer solution; adding the caspofungin compound and dissolving it; filtering the solution and lyophilizing.

27 Claims, 5 Drawing Sheets

Characteristic absorption peak for impurity RRT 1.35

Characteristic absorption peak for the compound of formula I

LOW IMPURITY CONTENT CASPOFUNGIN PREPARATION, METHOD FOR PREPARING SAME, AND USE THEREOF

TECHNICAL FIELD

The present invention relates to a pharmaceutical composition for treating and/or preventing fungal-infections, and the preparation method for the pharmaceutical composition.

BACKGROUND

The echinocandins are novel anti-fungal medicaments, which belong to 6-member ring compounds containing acetyl. Echinocandins are medicaments for inhibiting glucan synthetase and exert germicidal effect by non-competitively inhibiting the synthesis of -β(1,3)-D-glucan in cell-wall of fungi. Glucan is a polysaccharide in cell-wall of fungi, which is the important component in cell-wall and can maintain the integrity of cell-wall and the stability of osmotic pressure.

Caspofungin, the structure of which is shown in formula I, is the first anti-fungal medicament in echinocandins.

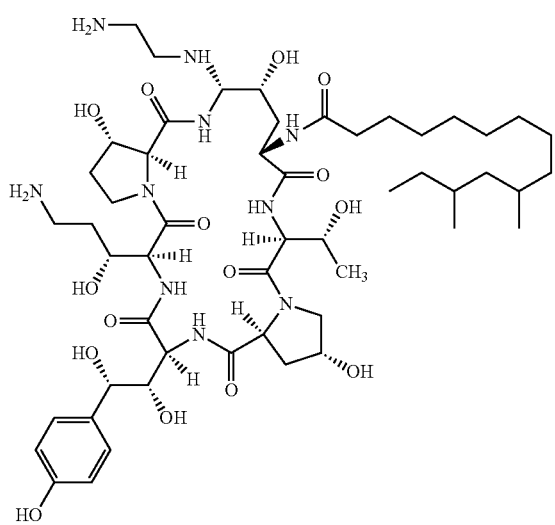

(I)

Caspofungin possesses broad-spectrum antifungal activities, demonstrating excellent antifungal activities toward fungi of *Candida albicans*, non-*Candida albicans* and *aspergillus*, and in vitro antifungal activities toward fungi, such as *Candida* and *aspergillus* etc., resistant to fluconazole, amphotericin B or fluorocytosine. Caspofungin does not possess cross-resistance with azoles or polyenes, no natural drug resistance exists in the isolates of *Candida*, and caspofungin applies to invasive aspergillosis to which other treatment is inefficient or intolerable.

Caspofungin preparation was firstly developed by Merck Sharp & Dohme (USA), marketed with the tradename "Cancidas", and in the preparation, caspofungin is administered in the form of caspofungin diacetate. Caspofungin has low stability, and is prone to degradation, thereby producing many degradation impurities. The degradation impurity at RRT (relative retention-time) 1.35 is a major impurity. And for the medication safety, the content of the impurity in "Cancidas" should be not more than 0.2% according to the quality standard of Cancidas stipulated by Merck Sharp & Dohme.

In U.S. Pat. No. 5,952,300 and U.S. Pat. No. 6,136,783, caspofungin pharmaceutical compositions comprising acetate buffer system and excipient and the indications thereof have been disclosed. In U.S. Pat. No. 5,952,300 and U.S. Pat. No. 6,136,783, it is disclosed that caspofungin pharmaceutical composition is stable due to the use of acetate buffer instead of tartrate buffer. However, the stability and degradation impurities for the composition have not been characterized or defined in detail. In US2010137197, another caspofungin pharmaceutical composition with better stability has been disclosed. The composition comprises one or more of non-reducing sugar with glass transition temperature over 90° C. and acetate buffer system at pH 5-7, therefore, the composition is better than the composition disclosed in U.S. Pat. No. 5,952,300 or U.S. Pat. No. 6,136,783 in stability. However, in US2010137197, the degradation impurity at RRT (relative retention-time) 1.35 from caspofungin (impurity RRT 1.35) has not been characterized or defined. According to the PDA (absorption spectrum) pattern, the degradation impurity RRT 1.35 has characteristic absorption peaks as shown in FIG. 4. Such peaks are similar to the characteristic absorption peaks of the compound of formula I as shown in FIG. 5.

In US20090324635, caspofungin free of impurity A (formula II), and preparation method thereof have been disclosed. In US20090291996, caspofungin free of impurity $C_0$ (formula III), preparation method and the pharmaceutical composition thereof have been disclosed. The degradation impurity of formula II and impurity RRT 1.35 have not been characterized or analysed in both of the documents whose contents relate to raw medicine. In US20090170753, another stable pharmaceutical composition comprising caspofungin has been disclosed, which comprises additional pH adjusting agent for caspofungin salt, the amount of which is less than 0.3 mole equivalent, and pharmaceutically acceptable amount of excipients for efficiently forming lyophilized cake. It is believed that the composition has better stability due to the minor amount of additional acetate pH adjusting agent. In US20090170753, the degradation impurity CAF-42 was determined, while impurity RRT 1.35 has not been characterized or defined. In CN102166186A, another caspofungin injectable composition, which is more stable, has been disclosed. The composition has better stability due to the existence of sorbitol or the mixture comprising sorbitol and other excipients. However, the inventors have tested the composition, and found that the stability of that composition is not as good as it was alleged and much lower than that of the formulation disclosed herein.

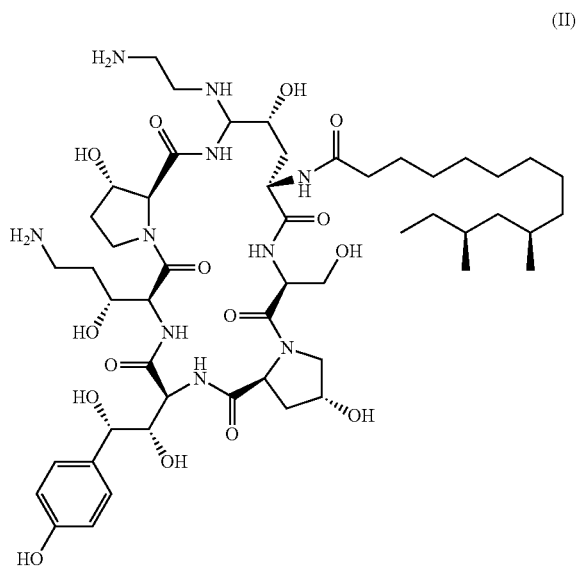

(II)

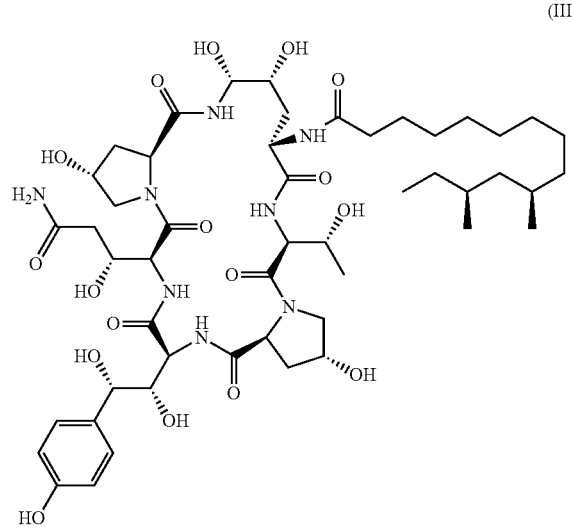

(III)

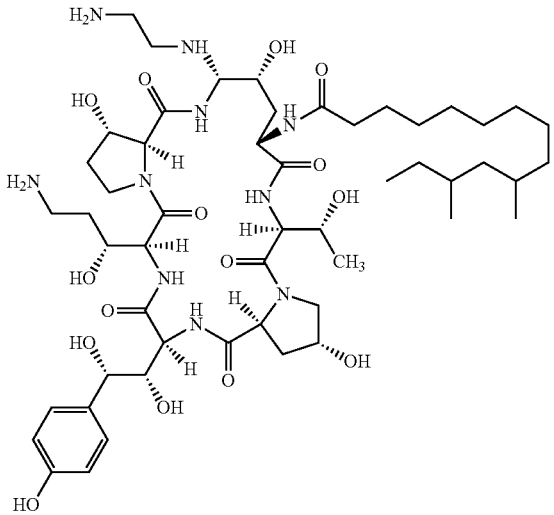

(I)

Impurities in an active pharmaceutical ingredient, such as caspofungin, are not desired, which may even do harm to the patient. However, it is impossible to remove all of the impurities. Therefore, it is important for a developer in pharmaceutical formulation field to reduce the content of impurities.

However, all of the pharmaceutical compositions known in the prior art are not desirable formulations, in which impurity RRT 1.35 is not strictly controlled. Therefore, it is necessary to develop a novel pharmaceutical composition and the preparation process thereof for reducing the HPLC content of impurity RRT 1.35 in caspofungin, improving the safety and stability thereof, and extending the shelf-life of medicament.

Upon lots of experiments, great advancements have been obtained in the stability of caspofungin pharmaceutical composition by the inventors.

In the present invention, a lyophilized pharmaceutical composition and the preparation method thereof have been provided. Said composition is of low-impurity, safe, stable, and reproducible, and can be directly used for treating/preventing fungal infections.

SUMMARY OF THE INVENTION

In the present invention, a pharmaceutical composition comprising the compound of formula I and/or the pharmaceutically acceptable salts thereof, wherein the HPLC content of impurity, the relative retention-time of which is about 1.35 under the following HPLC conditions, is not more than 0.10%.

In one embodiment, the HPLC content of impurity RRT 1.35 in the composition is not more than 0.05%.

In another embodiment, the pharmaceutically acceptable salt of the compound of formula I is an acid addition salt of organic acid or salt in other form.

In another embodiment, the pharmaceutical composition is a lyophilized formulation.

In another embodiment, the HPLC conditions are listed as follows:

High performance liquid chromatograph: WATERS 2695-2998

Column: YMC-Pack ODS-A column; Specification: 250× 4.6 mm, S-5 µm, 1.2 nm

Column temperature: 35° C.

Detection wavelength: 220 nm

Mobile phase:
A: 0.1% perchloric acid and 0.075% sodium chloride solution
B: acetonitrile Gradient conditions are shown in the below table:

| Time (Minute) | A % | B % |
|---|---|---|
| Begining | 65.5 | 34.5 |
| 14.5 | 65.5 | 34.5 |
| 35 | 50 | 50 |
| 45 | 35 | 65 |
| 50 | 20 | 80 |
| 52 | 20 | 80 |
| 53 | 65.5 | 34.5 |
| 66 | 65.5 | 34.5 |

Flow rate: 1.45 ml/min, the chromatograph system is adjusted for making the retention time of major peak around 20 min.

In the present invention, a pharmaceutical composition comprising the compound of formula I and/or the pharmaceutically acceptable salts thereof, wherein the composition comprises saccharide protective agent(s) and amino acid(s).

In one embodiment, the saccharide protective agent is one or more selected from the group consisting of sucrose, trehalose and mannitol.

In a further embodiment, the saccharide protective agent is sucrose.

In another embodiment, the amino acid is neutral amino acid.

In a further embodiment, the neutral amino acid is one or more selected from the group consisting of glycine, alanine, serine, tryptophan, tyrosine and threonine.

In a further embodiment, the neutral amino acid is glycine.

In one embodiment, the weight ratio of the saccharide protective agent to the compound of formula I or the pharmaceutically acceptable salts thereof is 60:1-2:1.

In a further embodiment, the weight ratio of the saccharide protective agent to the compound of formula I or the pharmaceutically acceptable salts thereof is 20:1-4:1.

In one embodiment, the weight ratio of the amino acid to the compound of formula I or the pharmaceutically acceptable salts thereof is 1:8-4:1.

In a further embodiment, the weight ratio of the amino acid to the compound of formula I or the pharmaceutically acceptable salts thereof is 1:4-1.5:1.

In the present invention, a method for preparing a pharmaceutical composition comprising the saccharide protective agent and the amino acid is provided, comprising the following steps:

a. dissolving the saccharide protective agent and the amino acid into prechilled water or suitable buffer solution;
b. adding the compound of formula I and dissolving it;
c. filtering the solution obtained in step b, and loading the filtrate into a vial under low temperature;
d. lyophilizing.

In one embodiment, the saccharide protective agent is one or more selected from the group consisting of sucrose, trehalose and mannitol.

In a further embodiment, the saccharide protective agent is sucrose.

In one embodiment, the amino acid is neutral amino acid.

In a further embodiment, the neutral amino acid is one or more selected from the group consisting of glycine, alanine, serine, tryptophan, tyrosine and threonine.

In a further embodiment, the neutral amino acid is glycine.

In one embodiment, the weight ratio of the saccharide protective agent to the compound of formula I is 60:1-2:1.

In a further embodiment, the weight ratio of the saccharide protective agent to the compound of formula I is 20:1-4:1.

In one embodiment, the weight ratio of the amino acid to the compound of formula I is 1:8-4:1.

In a further embodiment, the weight ratio of the amino acid to the compound of formula I is 1:4-1.5:1.

In one embodiment, in step d, the lyophilization process is that the composition is pre-frozen and subjected to the first-drying stage, and then to the second-drying stage with the temperature being maintained at 30° C.-40° C. for 5-20 hours, and the total period for lyophilization is not more than 52 hours.

In a further embodiment, during the second-drying stage, the temperature is maintained at 35° C. for 5-16 hours, and the total period for lyophilization is not more than 38 hours.

In one embodiment, in step d, the lyophilization process is:
a. the shelf temperature is continuously or discontinuously reduced to −45~−40° C. at a rate of 0.1~1° C./min;
b. the shelf temperature is maintained at −45~−40° C. for 12~180 mins;
c. the cold trap is turned on, and the temperature of cold trap is reduced below −45° C.;
d. the vacuum is applied, and the vacuum degree is reduced below 160 mTor;
e. the shelf temperature is continuously or discontinuously raised to −30~−10° C. at a rate of 0.1-1° C./min;
f. the shelf temperature is maintained at one or more temperatures from −30° C. to −10° C. for 960~1620 mins;
g. the shelf temperature is raised to 3~40° C. at a rate of 0.04~1° C./min;
h. the shelf temperature is maintained at 30~40° C. for 300~960 mins, and
i. upon lyophilization, a stopper is plugged into the vial, and the vial is removed out of the lyophilizer and capped.

In another embodiment, in step d, the lyophilization process is:
a. the shelf temperature is reduced to −40° C. at a rate of 1° C./min;
b. the shelf temperature is maintained at −40° C. for 120 mins;
c. the cold trap is turned on, and the temperature of cold trap is reduced below −45° C.;
d. the vacuum is applied, and the vacuum degree is reduced below 80 mTor;
e. the shelf temperature is raised to −20° C. at a rate of 0.1° C./min;
f. the shelf temperature is maintained at −20° C. for 540~840 mins;
g. the shelf temperature is raised to −10° C. at a rate of 0.1° C./min;
h. the shelf temperature is maintained at −10° C. for 420~780 mins;
i. the shelf temperature is raised to 30~40° C. at a rate of 0.04~1° C./min;
j. the shelf temperature is maintained at 30~40° C. for 300~960 mins, and
k. upon lyophilization, a stopper is plugged into the vial, and the vial is removed out of the lyophilizer and capped.

Alternatively, in step d, the lyophilization process is:
a. the shelf temperature is reduced to −5° C. at a rate of 1° C./min;
b. the shelf temperature is maintained at −5° C. for 30 mins;
c. the shelf temperature is reduced to −45° C. at a rate of 1° C./min;
d. the shelf temperature is maintained at −45° C. for 150 mins;
e. the cold trap is turned on, and the temperature of cold trap is reduced below −45° C.;
f. the vacuum is applied, and the vacuum degree is reduced below 160 mTor;
g. the shelf temperature is raised to −30° C. at a rate of 0.1° C./min;
h. the shelf temperature is maintained at −30° C. for 960 mins;
i. the shelf temperature is raised to 35° C. at a rate of 1° C./min;
j. the shelf temperature is maintained at 35° C. for 300 mins;
k. the vacuum degree is reduced below 20 mTor;
l. the shelf temperature is maintained at 35° C. for 300 mins, and
m. upon lyophilization, a stopper is plugged into the vial, and the vial is removed out of the lyophilizer and capped.

The use of any one of the above pharmaceutical compositions in the preparation of medicaments for preventing and/or treating fungal infections in mammals is also provided in the invention.

| Peak Name | Retension time (min) | % Area |
|---|---|---|
| Caspofungin | 19.950 | 97.83 |
| Impurity RRT 1.35 | 26.790 | 0.17 |

Figure 2:
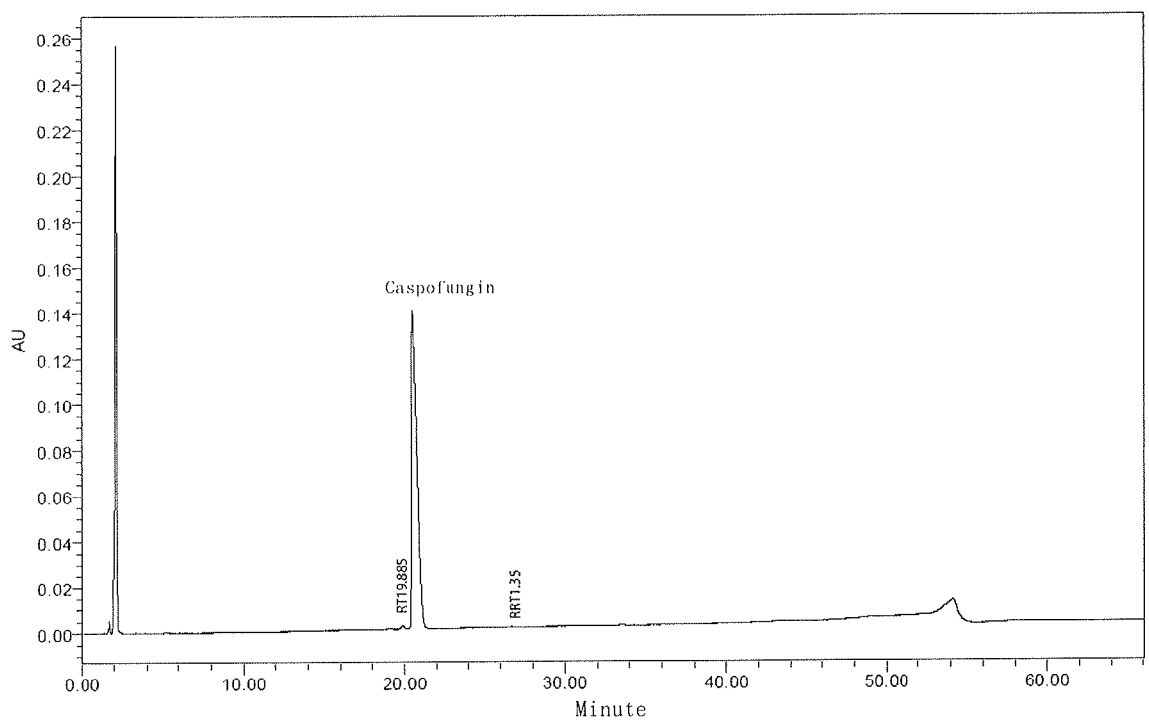

FIG. 2 shows the HPLC pattern for Formulation 3 in Examples after being stored at 25° C. for 24 weeks.

| Peak Name | Retension time (min) | % Area |
|---|---|---|
| Caspofungin | 20.496 | 99.14 |
| Impurity RRT 1.35 | 27.448 | 0.08 |

Figure 3:
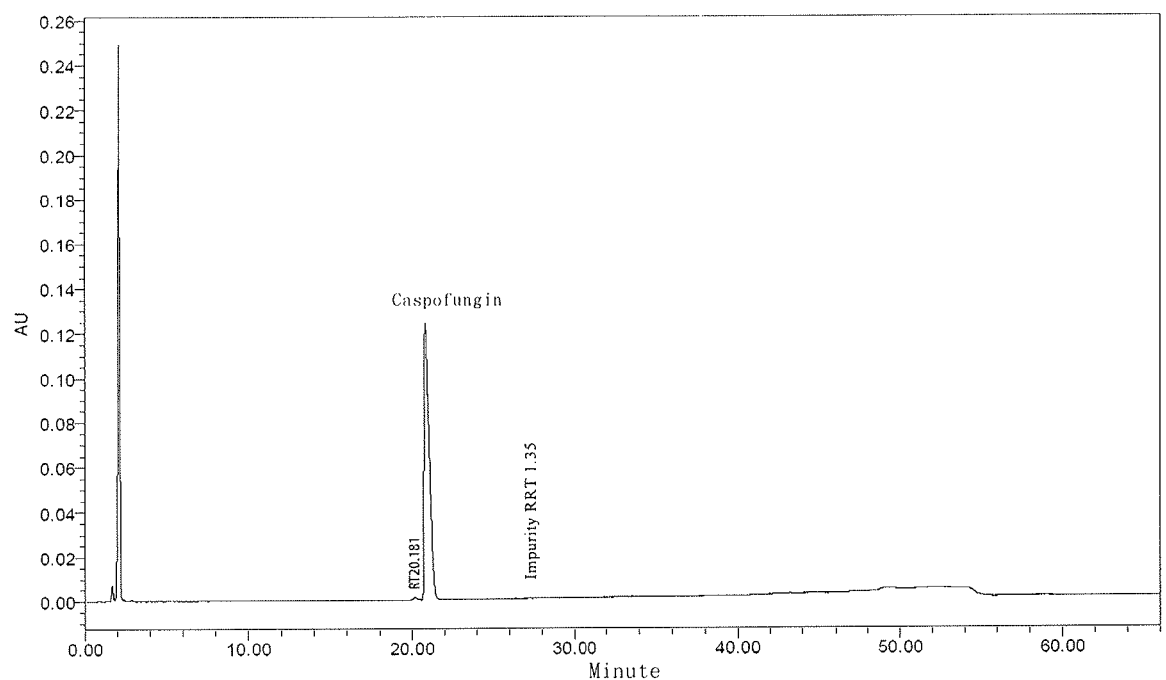

FIG. 3 shows the HPLC pattern for Formulation 3 in Examples after being stored at 2-8° C. for 24 weeks.

| Peak Name | Retension time (min) | % Area |
|---|---|---|
| Caspofungin | 20.829 | 99.24 |
| Impurity RRT 1.35 | 27.912 | 0.04 |

Figure 4:
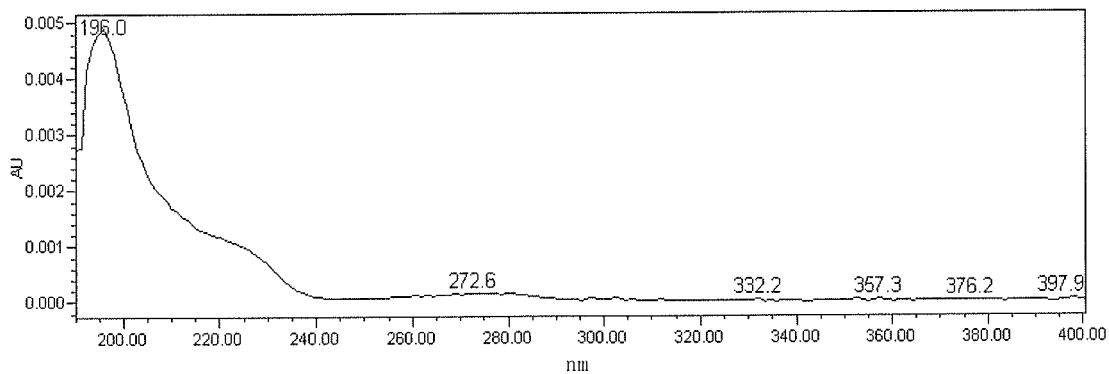

FIG. 4 shows the characteristic absorption peaks of impurity RRT 1.35.

Figure 5:
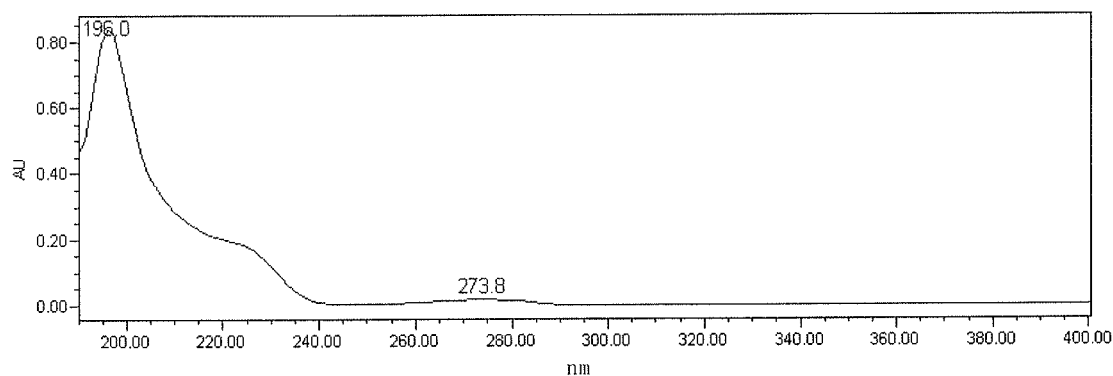

FIG. 5 shows the characteristic absorption peaks of the compound of formula I.

MODES FOR CARRYING OUT THE INVENTION

The inventors have tested various excipients during the study of chemical stability for anti-fungal compound, caspofungin which is an echinocandin, and studied the relationship between the content of excipients and the stability of compositions comprising caspofungin. It is unexpectedly found that the stability of pharmaceutical compositions comprising caspofungin or the pharmaceutically acceptable salts and saccharide protective agent as well as amino acid is excellent, even better than that of any reported composition comprising the compound, and the content of degradation impurities from caspofungin can be effectively controlled. Thus, the present invention has been accomplished.

As used herein, the term "relative retention-time (RRT)" means the ratio of retention time of a peak to that of the major peak under certain HPLC condition. For example, under certain HPLC condition, if the retention time of the major peak is 1 min, while the retention time of another peak is 2 min, the relative retention-time (RRT) for the latter is 2. Accordingly, impurity RRT 1.35 described herein is the impurity, the relative retention-time of which is 1.35 under the HPLC conditions described herein.

As used herein, the term "prechill" means such a process, during which the water in a liquid product is solidified for being sublimated in vacuum. "First-drying" means such a process, during which the free water between solutes can be removed by heating the product and the ice in solid state is sublimated into steam. During this stage, about 90% of water can be removed. "Second-drying", also called "desorption drying", means such a process, during which part of bound water inside the product is removed by further increasing the heating temperature after most of the ice in the product is sublimated, thereby the water content of the product reaching the standard. The increased temperature during this process will be in favor of improving the work efficiency. However, for the routine lyophilization, the temperature during the second-drying stage is maintained at relatively low level, such as 25° C., even 15° C., due to the poor thermal stability of caspofungin acetate, thereby resulting in some negative consequences, such as long total period for lyophilization. Compared with the routine method, higher temperature for second-drying stage with certain heating rate is employed in the lyophlization method according to the present invention, thereby reducing the formation of impurities and improving the work efficiency.

In one embodiment, Cancidas, commercially available product for caspofungin, was analyzed by HPLC, and it was found that Cancidas comprises 0.17% area ratio of degradation impurity RRT 1.35. Degradation impurity RRT 1.35 is the thermal degradation impurity from caspofungin, the degradation process of which is greatly influenced by temperature. Said impurity RRT 1.35 will readily be produced during the preparation and storage of caspofungin pharmaceutical composition.

Degradation of caspofungin can be avoided and the stability of the pharmaceutical composition can be improved by using the pharmaceutical composition and the preparation method thereof provided by the present invention.

In the present invention, a pharmaceutical composition comprising the compound of formula I and/or the pharmaceutically acceptable salts thereof is provided, wherein HPLC content of degradation impurity RRT 1.35 in the composition is not more than 0.10%; preferably, not more than 0.05%.

In the composition according to the present invention, the HPLC relative retention-time (RRT) of degradation impurity RRT 1.35 is 1.32-1.37.

The pharmaceutical composition provided by the present invention comprises:

a) caspofungin of formula I or the pharmaceutically acceptable salts thereof, and b) saccharide protective agent(s) and amino acid(s).

The amino acid is preferably neutral amino acid; more preferably, one or more selected from the group consisting of glycine, alanine, serine, tryptophan, tyrosine and threonine; most preferably, glycine.

The saccharide protective agent is one or more selected from the group consisting of sucrose, trehalose and mannitol; preferably, sucrose.

The pharmaceutical composition provided by the present invention can further comprise an additional pH adjusting agent, for example, pharmaceutically acceptable pH adjusting agent, such as phosphate buffer, acetate buffer, and citrate buffer. The pH range of the buffer is preferably 5-7; more preferably, 5.5-6.5.

Lyophilized powder can be obtained by lyophilizing the pharmaceutical composition provided by the invention. The lyophilized powder can be redissolved with aqueous solution, thereby obtaining liquid composition for parenteral, preferably intravenous administration.

Preferably, the aqueous solution is sterile water for injection, bacteriostasis water for injection optionally comprising methyl p-hydroxybenzoate and/or propyl p-hydroxybenzoate and/or 0.9% benzyl alcohol, normal saline or physiological saline, such as 0.9% sodium chloride solution, 0.45% or 0.225% sodium chloride solution, or Ringer's solution, and/or lactated Ringer's solution.

In the present invention, the use of the composition according to the invention is further provided for preparing medicaments, preferably intravenously administered medicaments for preventing and/or treating fungal infections or diseases caused by *Candida* sp. and/or *Aspergillus* sp. and/or *pneumocystis jiroveci* in mammals, preferably human.

The composition of the present invention can further comprise another component, such as one or more pharmaceutically acceptable excipients, including diluents or carriers well-known in the art which are suitable to be used in compositions intended to be parenterally administered, such as injectable pharmaceutical compositions for intramuscular, subcutaneous, intravenous, or intraperitoneal administration. Such excipient can include, for example, antioxidant, tonicity-adjusting agent, preservative, carbonhydrate, wax, water-soluble and/or swellable polymer, hydrophilic and/or hydrophobic material, gelatin, oil, solvent, water, and the like.

Suitable solvents or diluents include (but not limited to) aqueous solvent, preferably, bacteriostasis water for injection comprising methyl p-hydroxybenzoate and/or propyl p-hydroxybenzoate and/or 0.9% benzyl alcohol, normal saline or physiological saline, such as 0.9% sodium chloride solution, 0.45% or 0.225% sodium chloride solution, or Ringer's solution, and/or lactated Ringer's solution. The solvents and/or diluents can also be used to redissolve the composition of the invention in the form of lyophilized powder and/or further dilute the redissolved solution thus obtained.

As used herein, the term "caspofungin" means free base of caspofungin, for example, the pharmaceutically acceptable salts of caspofungin as described in EP0620232. And the solvate and/or hydrate thereof are also included in the present invention.

As used herein, the term "the pharmaceutically acceptable salt of caspofungin" means non-toxic salt of caspofungin. Preferably, the pharmaceutically acceptable salt of caspofungin is acid addition salt formed with organic acid, and the organic acid can be selected from acetic acid, citric acid, tartaric acid, propionic acid, oxalic acid, malic acid, maleic acid, lactic acid, glutamic acid. Most preferably, the pharmaceutically acceptable salt of caspofungin is caspofungin diacetate.

As used herein, the term "neutral amino acid" means such an amino acid that, in the molecule, the number of basic "—$NH_2$" is identical with that of acidic "—COOH".

Preferably, in the composition according to the present invention, the weight ratio of the saccharide protective agent to caspofungin or the pharmaceutically acceptable salts thereof is 60:1-2:1; more preferably, 20:1-4:1.

Preferably, in the composition according to the present invention, the weight ratio of the amino acid to caspofungin or the pharmaceutically acceptable salts thereof is 1:8-4:1; more preferably, 1:4-1.5:1.

In the present invention, a method for preparing caspofungin pharmaceutical composition is further provided, wherein the content of degradation impurity RRT 1.35 is not more than 0.10% (HPLC), said method comprising the following steps:

a. dissolving the saccharide protective agent and the amino acid into prechilled water or suitable buffer solution;
b. adding the compound of formula I and dissolving it;
c. filtering the solution obtained in step b, loading the filtrate into a vial under low temperature, and performing lyophilization;
d. in the lyophilization process, the composition is pre-frozen and subjected to the first-drying stage, and then to the second-drying stage with the temperature being maintained at 30° C.-40° C. for 5-20 hours, and the total period for lyophilization is not more than 52 hours. Preferably, after the composition is pre-frozen and subjected to the first-drying stage, the temperature during the second-drying stage is maintained at 35° C. for 5-16 hours, and the total period for lyophilization is not more than 38 hours.

Caspofungin pharmaceutical composition should be dried sufficiently, since the composition is sensitive to moisture. Caspofungin is unstable under normal temperature and high temperature, and the stability of caspofungin pharmaceutical compositions disclosed in the prior art is undesirable under normal temperature and high temperature. Therefore, with respect to the routine lyophilization methods for caspofungin pharmaceutical composition, the temperature during the second-drying stage is generally maintained at lower temperature. As disclosed in US2010137197, the temperature during the second-drying stage is maintained at 15° C. or 25° C. at the most. Therefore, some negative factors will occur, such as low drying-efficiency, extended total period for lyophilization and the like for obtaining a final product with low water content, and the practical production will be adversely affected.

Based on lots of experiments, the inventors have unexpectedly found that the stability of the composition provided in the present invention is desirable under high temperature, therefore, for the lyophilization method, higher temperature can be employed during the second-drying stage, thereby reducing the time-consuming and providing the composition with excellent stability.

Based on the above, the major advantages of the present invention are:

1. Production of degradation impurity RRT 1.35 during the preparation and storage of caspofungin pharmaceutical composition can be reduced by using particular combinations of excipients;

2. Compared with the prior art, caspofungin pharmaceutical composition according to the present invention is stable under normal temperature, thereby facilitating the storage and transportation thereof;

3. Compared with the prior art, caspofungin pharmaceutical composition according to the present invention can be lyophilized under relatively high temperature, thereby accelerating the lyophilization procedure and facilitating the practical production.

EXAMPLE

HPLC analytical method for caspofungin:
High performance liquid chromatograph: WATERS 2695-2998
Analytical Column: YMC-Pack ODS-A column; Specification: 250×4.6 mm, S-5 μm, 1.2 nm
Column temperature: 35° C.
Detection wavelength: 220 nm
Mobile phase:
A: 0.1% perchloric acid (analytically pure, Shanghai Jinlu Chemical Co., Ltd.) and 0.075% sodium chloride (analytically pure, Sinopharm Cheimical Reagent Co., Ltd) solution (1.0 ml of perchloric acid and 0.75 g of sodium chloride are dissolved in water and diluted to 1000 ml)
B: acetonitrile (HPLC grade, TEDIA)
Gradient conditions are shown in the below table:

| Time (Minute) | A % | B % |
|---|---|---|
| Begining | 65.5 | 34.5 |
| 14.5 | 65.5 | 34.5 |
| 35 | 50 | 50 |
| 45 | 35 | 65 |
| 50 | 20 | 80 |

-continued

| Time (Minute) | A % | B % |
|---|---|---|
| 52 | 20 | 80 |
| 53 | 65.5 | 34.5 |
| 66 | 65.5 | 34.5 |

Flow rate: 1 ml/min or 1.45 ml/min. When the flow rate is 1.45 ml/min, the retention time of major peak is around 20 min, which is identical with those reported in literatures, such as US2010/0137197, therefore, RRT value is determined under 1.45 ml/min of flow rate. By comparing the pattern for the flow rate 1 ml/min with the pattern for the flow rate of 1.45 ml/min, the peak at RRT 1.35 for the flow rate of 1.45 ml/min corresponds to the peak at RRT 1.26 for the flow rate of 1 ml/min.

% Relative Peak Area, i.e., HPLC content, means the percentage of peak area for a peak in total peak area.

Comparative Example 1

HPLC Analysis of Commercially Available Product of Caspofungin, "Cancidas"

Before expiration date, Cancidas, marketed caspofungin formulation (Merck Sharp & Dohme, USA), was analyzed for the impurities according to the above HPLC analytical method for caspofungin. Cancidas was diluted to 0.1 mg/ml with acetonitrile and 0.01 mol/L sodium acetate solution (1:4), and injected into the above HPLC system at 5° C. The content of impurity RRT 1.35 in Cancidas was shown in the following table:

| Lot Num | Caspofungin/% Relative Peak Area | Content of impurity RRT 1.35, % HPLC Relative Peak Area |
|---|---|---|
| K3625 | 97.66 | 0.16 |
| R1571 | 97.83 | 0.17 |

Comparative Example 2

All of the raw material used in the following comparative examples and examples are produced by SHANGHAI TECHWELL BIOPHARMACEUTICAL CO., LTD.

The composition was prepared according to Example 1 of US2010/0137197. 1.20 g of trehalose was dissolved into 3 ml of water, and then 7.5 µl of glacial acetic acid was added. The pH of the obtained solution was adjusted to 5.1 with 1 M of aqueous NaOH, and then 0.223 g of caspofungin acetate was added and dissolved with gentle agitating. The pH of the obtained solution was adjusted to 6.0 with 1 M of aqueous NaOH. The volume of the solution was adjusted to 5 mL with water. The resulting solution was filtrated with 0.22 µm membrane. The components of the composition (formulation 1) prior to lyophilization are shown in the following table:

| Caspofungin acetate (Based on caspofungin base, F. Ast) | 40 mg/ml |
|---|---|
| trehalose | 240 mg/ml |
| glacial acetic acid | 1.5 mg/ml |
| NaOH | Adjusting pH to 6.0 |

The solution was filled into 2 ml antibiotic vials in 0.5 ml/vial. V50 4405/50 Grey Sil A rubber stoppers (purchased from West Pharmaceutical Services, Inc) dried at 110° C. overnight were plugged into the vials, and then the vials were placed in plates and placed into lyophilizer for freeze-drying. The freeze-drying procedure (procedure F) is listed as follows:

a. the shelf temperature is reduced to −40° C. at a rate of 0.2° C./min;
 b. the shelf temperature is maintained at −40° C. for 120 mins;
 c. the cold trap is turned on, and the temperature of cold trap is reduced below −45° C.;
 d. the vacuum is applied, and the vacuum degree is reduced below 80 mTor;
 e. the shelf temperature is raised to −20° C. at a rate of 0.1° C./min;
 f. the shelf temperature is maintained at −20° C. for 3000 mins;
 g. the shelf temperature is raised to −15° C. at a rate of 0.1° C./min;
 h. the shelf temperature is maintained at −15° C. for 900 mins;
 i. the shelf temperature is raised to −10° C. at a rate of 0.1° C./min;
 j. the shelf temperature is maintained at −10° C. for 400 mins;
 k. the shelf temperature is raised to −5° C. at a rate of 0.1° C./min;
 l. the shelf temperature is maintained at −5° C. for 400 mins;
 m. the shelf temperature is raised to 15° C. at a rate of 0.1° C./min;
 n. the shelf temperature is maintained at 15° C. for 720 mins;
 o. the shelf temperature is raised to 25° C. at a rate of 1° C./min;
 p. the shelf temperature is maintained at 25° C. for 240 mins;
 q. upon lyophilization, the stopper is plugged into the vial, and then the vial is removed out of the lyophilizer and capped.

The lyophilized preparations were stored at 40° C., 75% RH for stability test, and sampled at week 8 and 24 for HPLC analysis. The lyophilized preparations were also stored at 25° C., 60% RH and 2-8° C. for stability test respectively, and sampled at week 12 for HPLC analysis (including data obtained at time 0).

Comparative Example 3

The composition was prepared according to Example 4 of CN101516387A. 0.5 g of mannitol and 0.75 g of sucrose were dissolved into 20 ml of water, and then 1.05 g of caspofungin base, i.e., 1.17 g of caspofungin acetate was added without adjusting pH. The final volume of the solution was adjusted to 25 mL with water. The resulting solution was filtrated with 0.22 µm membrane. The composition (formulation 2) prior to lyophilization is shown in the following table:

| Caspofungin acetate | 42 mg/ml |
|---|---|
| sucrose | 30 mg/ml |
| mannitol | 20 mg/ml |

The solution was filled into vials in 1.25 ml/vial (The freeze-drying procedure is the same as that for formulation 1, except that lyophilization is terminated after the shelf temperature is raised to 15° C., and the temperature will not be raised to 25° C.).

The lyophilized preparations were stored at 40° C., 75% RH for stability test, and sampled at week 8 and 24 for HPLC analysis. The lyophilized preparations were also stored at 25° C., 60% RH and 2-8° C. for stability test respectively, and sampled at week 12 for HPLC analysis (including data obtained at time 0).

Example 1

Preparation of Caspofungin Pharmaceutical Composition

The composition was prepared as follows: the saccharide protective agent and glycine (or other amino acids) were dissolved into water or solution comprising optional pH adjusting agent, and then the compound of formula I or the pharmaceutically acceptable salts was added and dissolved. The volume of the solution was adjusted to a certain volume, and then the obtained solution was lyophilized.

Different formulations were obtained by changing the concentration of caspofungin and/or saccharide protective agent and/or glycine (or other amino acids), and pH or concentration of pH adjusting agent. The composition of each formulation prior to lyophilization is shown in the following table:

| formulation No. | caspofungin mg/ml | saccharide protective agent 1 | saccharide protective agent 1 mg/ml | saccharide protective agent 2 | saccharide protective agent 2 mg/ml | Amino acid | Amino acid mg/ml | pH adjusting agent (pH) | Weight ratio of saccharide protective agent to caspofungin | Weight ratio of amino acid to caspofungin | lyophilization procedure |
|---|---|---|---|---|---|---|---|---|---|---|---|
| 3 | 40 | sucrose | 160 | none | 0 | glycine | 20 | 10 mM phosphate (pH 6.0) | 4:1 | 1:2 | A |
| 4 | 40 | sucrose | 240 | none | 0 | glycine | 60 | 10 mM phosphate (pH 5.5) | 6:1 | 1.5:1 | A |
| 5 | 5 | sucrose | 300 | none | 0 | glycine | 20 | 10 mM phosphate (pH 6.0) | 60:1 | 4:1 | F |
| 6 | 40 | sucrose | 160 | none | 0 | glycine | 40 | 0.4 mM citrate (pH 6.0) | 4:1 | 1:1 | E |
| 7 | 40 | sucrose | 200 | none | 0 | glycine | 20 | 25 mM acetate (pH 5.5) | 5:1 | 1:2 | A |
| 8 | 40 | sucrose | 160 | none | 0 | glycine | 40 | None | 4:1 | 1:1 | B |
| 9 | 40 | sucrose | 80 | none | 0 | glycine | 10 | 10 mM phosphate (pH 6.5) | 2:1 | 1:4 | C |
| 10 | 40 | sucrose | 50 | none | 0 | glycine | 40 | 25 mM acetate (pH 6.0) | 5:4 | 1:1 | D |
| 11 | 40 | sucrose | 200 | none | 0 | glycine | 5 | 10 mM phosphate (pH 6.0) | 5:1 | 1:8 | D |
| 12 | 40 | sucrose | 240 | none | 0 | None | 0 | none | 6:1 | 0 | A |
| 13 | 40 | trehalose | 240 | none | 0 | glycine | 20 | 10 mM phosphate (pH 6.0) | 4:1 | 1:2 | E |
| 14 | 40 | mannitol | 60 | none | 0 | glycine | 20 | 10 mM phosphate (pH 6.0) | 4:1 | 1:2 | E |
| 15 | 40 | sucrose | 30 | mannitol | 20 | glycine | 20 | 10 mM phosphate (pH 6.0) | 4:1 | 1:2 | E |
| 16 | 40 | trehalose | 240 | mannitol | 20 | glycine | 20 | 10 mM phosphate (pH 6.0) | 4:1 | 1:2 | E |
| 17 | 30 | sucrose | 600 | none | 0 | alanine | 20 | 10 mM phosphate (pH 6.0) | 20:1 | 2:3 | A |
| 18 | 40 | sucrose | 160 | none | 0 | serine | 60 | 10 mM phosphate (pH 6.0) | 4:1 | 1.5:1 | A |
| 19 | 40 | sucrose | 80 | none | 0 | tryptophan | 160 | 10 mM phosphate (pH 6.0) | 2:1 | 4:1 | A |
| 20 | 40 | sucrose | 160 | none | 0 | tyrosine | 5 | 10 mM phosphate (pH 6.0) | 4:1 | 1:8 | A |
| 21 | 40 | sucrose | 160 | none | 0 | threonine | 20 | 10 mM phosphate (pH 6.0) | 4:1 | 1:2 | A |

Each lyophilization procedure is listed as follows:

Lyophilization Procedure A:
a. the shelf temperature is reduced to −40° C. at a rate of 1° C./min;
b. the shelf temperature is maintained at −40° C. for 120 mins;
c. the cold trap is turned on, and the temperature of cold trap is reduced below −45° C.;
d. the vacuum is applied, and the vacuum degree is reduced below 80 mTor;
e. the shelf temperature is raised to −20° C. at a rate of 0.1° C./min;
f. the shelf temperature is maintained at −20° C. for 540 mins;
g. the shelf temperature is raised to −10° C. at a rate of 0.1° C./min;
h. the shelf temperature is maintained at −10° C. for 420 mins;
i. the shelf temperature is raised to 35° C. at a rate of 0.1° C./min;
j. the shelf temperature is maintained at 35° C. for 960 mins;
k. upon lyophilization, the stopper is plugged into the vial, and then the vial is removed out of the lyophilizer and capped.

Lyophilization Procedure B:
a. the shelf temperature is reduced to −40° C. at a rate of 1° C./min;
b. the shelf temperature is maintained at −40° C. for 120 mins;
c. the cold trap is turned on, and the temperature of cold trap is reduced below −45° C.;
d. the vacuum is applied, and the vacuum degree is reduced below 80 mTor;
e. the shelf temperature is raised to −20° C. at a rate of 0.1° C./min;
f. the shelf temperature is maintained at −20° C. for 540 mins;
g. the shelf temperature is raised to −10° C. at a rate of 0.1° C./min;
h. the shelf temperature is maintained at −10° C. for 420 mins;
i. the shelf temperature is raised to 35° C. at a rate of 0.04° C./min;
j. the shelf temperature is maintained at 35° C. for 300 mins;
k. upon lyophilization, the stopper is plugged into the vial, and then the vial is removed out of the lyophilizer and capped.

Lyophilization Procedure C:
a. the shelf temperature is reduced to −40° C. at a rate of 0.1° C./min;
b. the shelf temperature is maintained at −40° C. for 120 mins;
c. the cold trap is turned on, and the temperature of cold trap is reduced below −45° C.;
d. the vacuum is applied, and the vacuum degree is reduced below 80 mTor;
e. the shelf temperature is raised to −20° C. at a rate of 0.1° C./min;
f. the shelf temperature is maintained at −20° C. for 840 mins;
g. the shelf temperature is raised to −10° C. at a rate of 0.1° C./min;
h. the shelf temperature is maintained at −10° C. for 780 mins;
i. the shelf temperature is raised to 30° C. at a rate of 0.1° C./min;
j. the shelf temperature is maintained at 30° C. for 600 mins;
k. upon lyophilization, the stopper is plugged into the vial, and then the vial is removed out of the lyophilizer and capped.

Lyophilization Procedure D:
a. the shelf temperature is reduced to −40° C. at a rate of 1° C./min;
b. the shelf temperature is maintained at −40° C. for 120 mins;
c. the cold trap is turned on, and the temperature of cold trap is reduced below −45° C.;
d. the vacuum is applied, and the vacuum degree is reduced below 80 mTor;
e. the shelf temperature is raised to −20° C. at a rate of 0.1° C./min;
f. the shelf temperature is maintained at −20° C. for 700 mins;
g. the shelf temperature is raised to −10° C. at a rate of 0.1° C./min;
h. the shelf temperature is maintained at −10° C. for 660 mins;
i. the shelf temperature is raised to 40° C. at a rate of 0.1° C./min;
j. the shelf temperature is maintained at 40° C. for 600 mins;
k. upon lyophilization, the stopper is plugged into the vial, and then the vial is removed out of the lyophilizer and capped.

Lyophilization Procedure E:
a. the shelf temperature is reduced to −5° C. at a rate of 1° C./min;
b. the shelf temperature is maintained at −5° C. for 30 mins;
c. the shelf temperature is reduced to −45° C. at a rate of 1° C./min;
d. the shelf temperature is maintained at −45° C. for 150 mins; e. the cold trap is turned on, and the temperature of cold trap is reduced below −45° C.;
f. the vacuum is applied, and the vacuum degree is reduced below 160 mTor;
g. the shelf temperature is raised to −30° C. at a rate of 0.1° C./min;
h. the shelf temperature is maintained at −30° C. for 960 mins;
i. the shelf temperature is raised to 35° C. at a rate of 1° C./min;
j. the shelf temperature is maintained at 35° C. for 300 mins;
k. the vacuum degree is reduced below 20 mTor;
l. the shelf temperature is maintained at 35° C. for 300 mins;
m. upon lyophilization, the stopper is plugged into the vial, and then the vial is removed out of the lyophilizer and capped.

After lyophilization, each formulation was tested for stability according to Comparative Example 2.

Example 2

0.75 g of sorbitol and 0.5 g of mannitol were dissolved into 20 ml of water, and then 1.05 g of caspofungin base was added. Then, sodium dihydrogen phosphate was added until the final concentration thereof was 20 mM. The pH of the obtained solution was adjusted to 6.0 with aqueous NaOH. The final volume of the solution was adjusted to 25 mL with water. The resulting solution was filtrated with 0.22 μm membrane. The components of the composition (formulation 22) prior to lyophilization are shown in the following table:

| Caspofungin base | 42 mg/ml |
|---|---|
| Sorbitol | 30 mg/ml |
| mannitol | 20 mg/ml |
| sodium dihydrogen phosphate | 20 mM |
| NaOH | Adjusting pH to 6.0 |

The solution was filled into vials in 1.25 ml/vial and lyophilized.

The lyophilized preparations were stored at 40° C. for stability test, and sampled at week 8 and 24 for HPLC analysis, respectively. The lyophilized preparations were also stored at 25° C., 65% RH and 2-8° C. for stability test, respectively, and sampled at week 24 for HPLC analysis (including data obtained at time 0).

Example 3

Stability of Caspofungin Pharmaceutical Composition

The samples from Comparative Example 2, 3 and 4 as well as Example 1 were tested for stability by HPLC analysis.

Results from 40° C.-stability experiment are listed in the following table:

| Formulation No. | Temperature ° C. | Caspofungin/ % relative peak area time 0 | Caspofungin/ % relative peak area week 8 | Caspofungin/ % relative peak area week 24 |
|---|---|---|---|---|
| 1 | 40 | 99.17 | 94.22 | 85.98 |
| 2 | 40 | 99.10 | 87.39 | 79.31 |
| 3 | 40 | 99.29 | 98.83 | 97.76 |
| 4 | 40 | 99.26 | 98.79 | 97.91 |
| 5 | 40 | 99.25 | 98.82 | 97.93 |
| 6 | 40 | 99.27 | 98.77 | 97.93 |
| 7 | 40 | 99.24 | 98.72 | 97.87 |
| 8 | 40 | 99.25 | 98.76 | 97.95 |
| 9 | 40 | 99.27 | 98.65 | 97.88 |
| 10 | 40 | 99.26 | 98.82 | 97.97 |
| 11 | 40 | 99.25 | 98.70 | 97.82 |
| 12 | 40 | 99.20 | 97.83 | 96.75 |
| 13 | 40 | 99.23 | 98.37 | 96.86 |
| 14 | 40 | 99.25 | 98.08 | 96.24 |
| 15 | 40 | 99.26 | 98.63 | 97.57 |
| 16 | 40 | 99.23 | 98.53 | 97.52 |
| 17 | 40 | 99.27 | 98.79 | 97.87 |
| 18 | 40 | 99.25 | 98.82 | 97.93 |
| 19 | 40 | 99.22 | 98.71 | 97.78 |
| 20 | 40 | 99.24 | 98.67 | 97.65 |
| 21 | 40 | 99.27 | 98.71 | 97.72 |
| 22 | 40 | 99.13 | 88.23 | 81.44 |

After being stored at 40° C., % relative peak area of caspofungin significantly decreased, impurity situation is complex, and it is of no significance to compare a single impurity, therefore, the data regarding impurity RRT 1.35 are not shown.

Results from 25° C.-stability experiment are listed in the following table:

| Formulation No. | caspofungin/ % Relative Peak Area | | Impurity RRT 1.35/ % Relative peak area | |
|---|---|---|---|---|
| | Time 0 | Week 24 | Time 0 | Week 24 |
| 1 | 99.17 | 97.26 | 0.11 | 0.25 |
| 2 | 99.10 | 96.75 | 0.13 | 0.27 |
| 3 | 99.27 | 99.14 | 0.01 | 0.08 |
| 4 | 99.26 | 99.15 | 0.02 | 0.08 |
| 5 | 99.25 | 99.17 | 0.02 | 0.13 |
| 6 | 99.27 | 99.14 | 0.03 | 0.07 |
| 7 | 99.24 | 99.17 | 0.02 | 0.10 |
| 8 | 99.25 | 99.13 | 0.02 | 0.07 |
| 9 | 99.27 | 99.15 | 0.02 | 0.09 |
| 10 | 99.26 | 99.16 | 0.01 | 0.09 |
| 11 | 99.25 | 99.11 | 0.01 | 0.13 |
| 12 | 99.20 | 98.91 | 0.11 | 0.23 |
| 13 | 99.23 | 99.13 | 0.02 | 0.07 |
| 14 | 99.25 | 99.10 | 0.02 | 0.08 |
| 15 | 99.26 | 99.14 | 0.01 | 0.10 |
| 16 | 99.23 | 99.13 | 0.02 | 0.10 |
| 17 | 99.20 | 99.16 | 0.02 | 0.08 |
| 18 | 99.25 | 99.12 | 0.01 | 0.07 |
| 19 | 99.22 | 99.05 | 0.02 | 0.09 |
| 20 | 99.24 | 99.09 | 0.02 | 0.08 |
| 21 | 99.27 | 99.11 | 0.02 | 0.10 |
| 22 | 99.13 | 97.15 | 0.12 | 0.25 |

Results from 2-8° C.-stability experiment are listed in the following table:

| Formulation No. | Caspofungin/ % Relative Peak Area | | Impurity RRT 1.35/ % Relative Peak Area | |
|---|---|---|---|---|
| | Time 0 | Week 24 | Time 0 | Week 24 |
| 1 | 99.17 | 99.11 | 0.11 | 0.13 |
| 2 | 99.10 | 98.99 | 0.13 | 0.14 |
| 3 | 99.29 | 99.24 | 0.01 | 0.04 |
| 4 | 99.26 | 99.23 | 0.02 | 0.04 |
| 5 | 99.25 | 99.24 | 0.02 | 0.05 |
| 6 | 99.27 | 99.20 | 0.03 | 0.04 |
| 7 | 99.24 | 99.23 | 0.02 | 0.03 |
| 8 | 99.25 | 99.20 | 0.02 | 0.03 |
| 9 | 99.27 | 99.22 | 0.02 | 0.04 |
| 10 | 99.26 | 99.22 | 0.01 | 0.03 |
| 11 | 99.25 | 99.21 | 0.01 | 0.03 |
| 12 | 99.20 | 99.16 | 0.11 | 0.12 |
| 13 | 99.23 | 99.19 | 0.02 | 0.05 |
| 14 | 99.25 | 99.21 | 0.02 | 0.05 |
| 15 | 99.26 | 99.24 | 0.01 | 0.04 |
| 16 | 99.23 | 99.20 | 0.02 | 0.05 |
| 17 | 99.20 | 99.13 | 0.01 | 0.03 |
| 18 | 99.25 | 99.17 | 0.02 | 0.05 |
| 19 | 99.22 | 99.12 | 0.02 | 0.07 |
| 20 | 99.24 | 99.18 | 0.01 | 0.05 |
| 21 | 99.27 | 99.22 | 0.02 | 0.04 |
| 22 | 99.13 | 99.04 | 0.12 | 0.13 |

From the above data obtained from stability experiments, it can be found that: each formulation comprising glycine is very stable at 2-8° C., and the content of caspofungin does not significantly decrease after 24 weeks. Among the formulations comprising one or two selected from the group consisting of sucrose, trehalose and mannitol as saccharide protective agent and glycine, the formulation comprising sucrose and glycine is the most stable. And the formulations comprising neutral amino acid, such as alanine, are relatively stable. In the present invention, 2-8° C. stability data are provided based on the raw medicine produced by the applicant which includes some impurities, such as impurity RRT (relative retention time) 0.95. Such impurities won't change during the stability test, therefore, won't affect the conclusion of stability. This is why caspofungin % relative peak area provided in CN101516387A is larger than the data provided in the present invention.

In CN101516387A, stable caspofungin pharmaceutical composition was disclosed, and the stability thereof was tested under 25° C. and 2-8° C., wherein the stability data at 2-8° C. were provided. At such temperature, the total content of impurities in each composition described in CN101516387A, compared with the data at time 0, decreases (not increases). However, such conclusion does not comply with scientific rules or results from measurement error. In comparative example 2, the best formulation of CN101516387A was simulated, and it was found that the stability of the formulation at 2-8° C. does not change significantly, however, at higher temperature, the stability of the formulation is significantly worse than that of the pharmaceutical composition provided in the present invention. Additionally, since for the formulation which is stable at 2-8° C., there are many difficulties in the practical production and transportation, the inventors made an effort to develop a formulation which is stable at normal temperature. From the above 40° C. and 25° C. stability-data, it can be found that the caspofungin pharmaceutical composition provided by the inventors possesses significant advantages in high-temperature stability. Additionally, after being stored at 25° C. for 24 weeks, the content of impurity RRT 1.35 in the pharmaceutical composition disclosed herein can be controlled below 0.1%, even below 0.05%.

Figure 1:
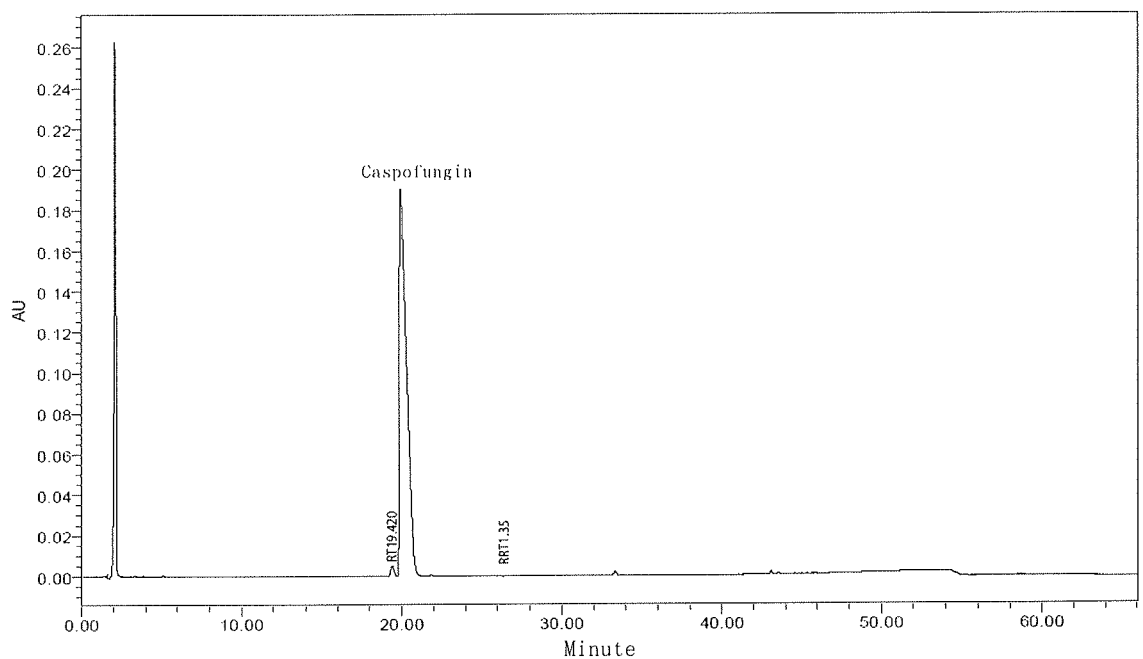
FIG. 1 shows the HPLC pattern for Cancidas R1571 in Comparative Example 1.

Additionally, formulation 1 is the comparative test conducted according to Example 1 of US2010/0137197. The stability data provided in US2010/0137197 is the percentage of the caspofungin content at certain time point to the caspofungin content at time 0, which will be influenced by difference in filling amount between vials, and the percentage will likely be more than 100%, which is demonstrated by the 30° C.-stability data from Example 2-2 shown in Table 3-C of US2010/0137197. Moreover, caspofungin % relative peak area at time 0 is less than 1, therefore, the data disclosed in US2010/0137197 will be greater than the value obtained in the present invention, thereby making the data disclosed in US2010/0137197 less comparable. Good stability of the formulation disclosed in US2010/0137197 is verified in the present invention. However, the caspofungin pharmaceutical composition disclosed herein significantly has better stability over that composition. The HPLC patterns of Cancidas R1571 and formulation 3 are shown in FIGS. 1-3.

Formulation 22 is the same as that disclosed in CN102166186A, and it is found that the stability of the formulation disclosed in CN102166186A is significantly worse than that of the formulation disclosed herein.

Caspofungin is extremely unstable under high temperature, therefore, with respect to the lyophilization methods for caspofungin pharmaceutical composition disclosed in the prior art, relatively low second-drying temperature and extended drying time are employed for achieving low content of water and impurities. The caspofungin pharmaceutical compositions provided by the present invention have better stability at normal temperature and high temperature, therefore, with respect to the lyophilization method for the compositions, higher temperature can be employed during the second-drying stage, so that the lyophilization efficiency can be improved and the total time-consuming will be not more than 52 hours, enen not more than 38 hours, the composition will have excellent stability, and the impurity content is significantly lower than that of the product obtained by lyophilizing caspofungin pharmaceutical composition in prior art according to the routine lyophilization method.

Descriptions hereinbefore are merely preferable examples and these examples are not to limit the scope of the invention. The virtual technical content of the present invention is broadly defined in the claims sought for protection of the present invention. Should any technical entity or method accomplished by anyone else be equivalent to the scope of protection defined by the present invention, it shall be deemed as an equivalent substitution, all of which shall be deemed as encompassed in the scope of claims of the present invention.

The invention claimed is:

1. A pharmaceutical composition comprising a compound of formula I or a pharmaceutically acceptable salt thereof, a saccharide protective agent, and an amino acid, wherein, in the composition, the content of an impurity, having a relative retention-time of about 1.35 is not more than 0.10%;

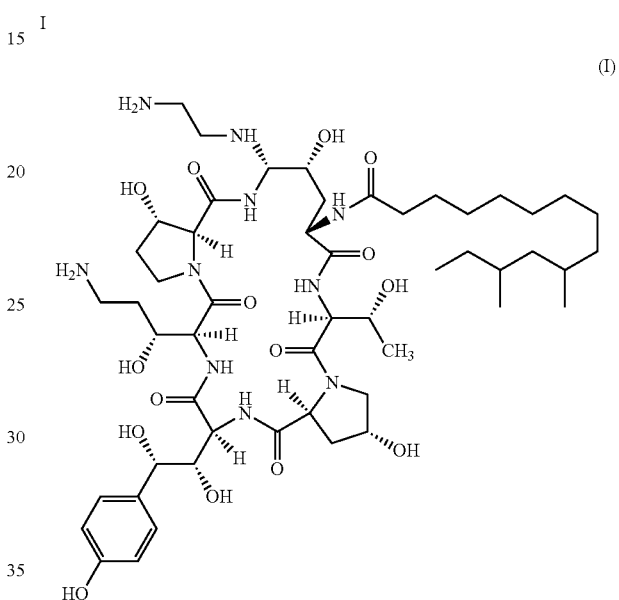

wherein the relative retention time is measured under HPLC conditions as follows:
  Analytical Column: YMC-Pack ODS-A column; Specification: 250×4.6 mm, S-5 μm, 1.2 nm, C18,
  Column temperature: 35° C.
  Detection wavelength: 220 nm
  Mobile phase:
  A: 0.1% perchloric acid and 0.075% sodium chloride solution
  B: acetonitrile
  Gradient conditions are shown in the below table:

| Time (Minute) | A % | B % |
|---|---|---|
| Beginning | 65.5 | 34.5 |
| 14.5 | 65.5 | 34.5 |
| 35 | 50 | 50 |
| 45 | 35 | 65 |
| 50 | 20 | 80 |
| 52 | 20 | 80 |
| 53 | 65.5 | 34.5 |
| 66 | 65.5 | 34.5 |

Flow rate: 1.45 ml/min, and wherein the chromatograph system is adjusted so the retention time of the compound major peak is around 20 min.

2. The pharmaceutical composition according to claim 1, wherein, in the composition, the content of the impurity, relative retention-time of which is about 1.35, is not more than 0.05%.

3. The pharmaceutical composition according to claim 1, wherein the pharmaceutically acceptable salt of the compound of formula I is an acid addition salt of an organic acid.

4. The pharmaceutical composition according to claim 1, wherein the pharmaceutical composition is a lyophilized formulation.

5. The pharmaceutical composition according to claim 1, wherein the saccharide protective agent is one or more selected from the group consisting of sucrose, trehalose and mannitol.

6. The pharmaceutical composition according to claim 5, wherein the saccharide protective agent is sucrose.

7. The pharmaceutical composition according to claim 1, wherein the amino acid is a neutral amino acid.

8. The pharmaceutical composition according to claim 7, wherein the neutral amino acid is one or more selected from the group consisting of glycine, alanine, serine, tryptophan, tyrosine and threonine.

9. The pharmaceutical composition according to claim 8, wherein the neutral amino acid is glycine.

10. The pharmaceutical composition according to claim 1, wherein the weight ratio of the saccharide protective agent to the compound of formula I or the pharmaceutically acceptable salt thereof is 60:1-2:1.

11. The pharmaceutical composition according to claim 10, wherein the weight ratio of the saccharide protective agent to the compound of formula I or the pharmaceutically acceptable salt thereof is 20:1-4:1.

12. The pharmaceutical composition according to claim 1, wherein the weight ratio of the amino acid to the compound of formula I or the pharmaceutically acceptable salt thereof is 1:8-4:1.

13. The pharmaceutical composition according to claim 12, wherein the weight ratio of the amino acid to the compound of formula I or the pharmaceutically acceptable salt thereof is 1:4-1.5:1.

14. A method for preparing the pharmaceutical composition according to claim 1, comprising:
   a. dissolving the saccharide protective agent and the amino acid into water or suitable buffer solution;
   b. adding the compound of formula I and dissolving it;
   c. filtering the solution obtained in step b, and loading the filtrate into a vial; and
   d. lyophilizing.

15. The method according to claim 14, wherein the saccharide protective agent is one or two selected from the group consisting of sucrose, trehalose and mannitol.

16. The method according to claim 15, wherein the saccharide protective agent is sucrose.

17. The method according to claim 14, wherein the amino acid is a neutral amino acid.

18. The method according to claim 17, wherein the neutral amino acid is one or more selected from the group consisting of glycine, alanine, serine, tryptophan, tyrosine and threonine.

19. The method according to claim 18, wherein the neutral amino acid is glycine.

20. The method according to claim 14, wherein the weight ratio of the saccharide protective agent to the compound of formula I is 60:1-2:1.

21. The method according to claim 20, wherein the weight ratio of the saccharide protective agent to the compound of formula I is 20:1-4:1.

22. The method according to claim 14, wherein the weight ratio of the amino acid to the compound of formula I is 1:8-4:1.

23. The method according to claim 22, wherein the weight ratio of the amino acid to the compound of formula I is 1:4-1.5:1.

24. The method according to claim 14, wherein, in step d, the composition is pre-frozen and subjected to a first drying stage, and then to a second drying stage, wherein the second drying stage is carried out at 30° C.-40° C. for 5-20 hours, and the total period for lyophilization is not more than 52 hours.

25. The method according to claim 24, wherein, during the second drying stage, the temperature is maintained at 35° C. for 5-16 hours, and the total period for lyophilization is not more than 38 hours.

26. The method according to claim 14, wherein, in step d, the lyophilization process is:
   a. a shelf temperature is continuously or discontinuously reduced to −45~−40° C. at a rate of 0.1~1° C./min;
   b. the shelf temperature is maintained at −45~−40° C. for 120~180 mins;
   c. a cold trap is turned on, and the temperature of the cold trap is reduced below −45° C.;
   d. a vacuum is applied, and the vacuum degree is reduced below 160 mTor;
   e. the shelf temperature is continuously or discontinuously raised to −30~−10° C. at a rate of 0.1-1° C./min;
   f. the shelf temperature is maintained at one or more temperatures from −30° C. to −10° C. for 960~1620 mins;
   g. the shelf temperature is raised to 30~40° C. at a rate of 0.04~1° C./min, and
   h. the shelf-temperature is maintained at 30~40° C. for 300~960 mins.

27. A method for preventing and/or treating fungal infection in a mammal, comprising administering the pharmaceutical composition according to claim 1 to a mammal in need thereof.

* * * * *

UNITED STATES PATENT AND TRADEMARK OFFICE
CERTIFICATE OF CORRECTION

| | | |
|---|---|---|
| PATENT NO. | : 9,149,502 B2 | Page 1 of 1 |
| APPLICATION NO. | : 14/346268 | |
| DATED | : October 6, 2015 | |
| INVENTOR(S) | : Yunhai Hong et al. | |

It is certified that error appears in the above-identified patent and that said Letters Patent is hereby corrected as shown below:

ON THE TITLE PAGE:

In the Assignee section, Item (73), assignee's name is misspelled as "Shanghai Techwell Biopharmaceuticals Co., Ltd." Please correct the assignee's name to read:

-- Shanghai Techwell Biopharmaceutical Co., Ltd. --

Signed and Sealed this
First Day of March, 2016

Michelle K. Lee
*Director of the United States Patent and Trademark Office*